US010550368B2

(12) United States Patent
Wang et al.

(10) Patent No.: US 10,550,368 B2
(45) Date of Patent: Feb. 4, 2020

(54) TISSUE PROCESSING DEVICE AND ASSOCIATED SYSTEMS AND METHODS

(71) Applicant: LifeCell Corporation, Madison, NJ (US)

(72) Inventors: Kai-Roy Wang, Jersey City, NJ (US); Aaron Barere, Hoboken, NJ (US); Evan J. Friedman, West Orange, NJ (US); Sangwook Park, Dunellen, NJ (US)

(73) Assignee: LIFECELL CORPORATION, Madison, NJ (US)

(*) Notice: Subject to any disclaimer, the term of this patent is extended or adjusted under 35 U.S.C. 154(b) by 0 days.

(21) Appl. No.: 16/229,787

(22) Filed: Dec. 21, 2018

(65) Prior Publication Data

US 2019/0119644 A1    Apr. 25, 2019

Related U.S. Application Data

(63) Continuation of application No. 15/047,034, filed on Feb. 18, 2016, now Pat. No. 10,184,111.

(60) Provisional application No. 62/118,192, filed on Feb. 19, 2015.

(51) Int. Cl.
| | | |
|---|---|---|
| *C12N 1/00* | (2006.01) | |
| *C12N 5/077* | (2010.01) | |
| *A61B 17/00* | (2006.01) | |
| *A61M 1/00* | (2006.01) | |
| *A61B 17/322* | (2006.01) | |
| *C12M 1/00* | (2006.01) | |

(52) U.S. Cl.
CPC ............ *C12N 5/0653* (2013.01); *A61B 17/00* (2013.01); *A61B 2017/00685* (2013.01); *A61B 2017/00902* (2013.01); *A61B 2017/00969* (2013.01); *A61B 2017/3225* (2013.01); *A61M 1/0056* (2013.01); *A61M 2202/08* (2013.01); *A61M 2205/103* (2013.01); *C12M 47/04* (2013.01)

(58) Field of Classification Search
CPC ........................................................ C12N 1/00
See application file for complete search history.

(56) References Cited

U.S. PATENT DOCUMENTS

| | | | |
|---|---|---|---|
| 4,753,634 | A | 6/1988 | Johnson |
| 4,834,703 | A | 5/1989 | Dubrul et al. |
| 5,591,187 | A | 1/1997 | Dekel |
| 5,786,207 | A | 7/1998 | Katz et al. |
| 5,913,859 | A | 6/1999 | Shapira |
| 6,071,284 | A | 6/2000 | Fox |
| 6,258,054 | B1 | 7/2001 | Mozsary et al. |

(Continued)

FOREIGN PATENT DOCUMENTS

| | | |
|---|---|---|
| WO | 2009/055610 A1 | 4/2009 |
| WO | 2012/019103 A2 | 2/2012 |

(Continued)

OTHER PUBLICATIONS

International Search and Written Opinion in related PCT/US2016/018444 dated May 19, 2016.

(Continued)

*Primary Examiner* — Jyoti Nagpaul
(74) *Attorney, Agent, or Firm* — McCarter & English, LLP

(57) ABSTRACT

Tissue processing devices are provided. The tissue processing devices can be used to process and transport tissue in a closed and continuous environment. The devices can be used for adipose tissue transfer, including autologous fat grafting.

20 Claims, 4 Drawing Sheets

(56) References Cited

U.S. PATENT DOCUMENTS

| | | |
|---|---|---|
| 7,588,732 B2 | 9/2009 | Buss |
| 7,651,684 B2 | 1/2010 | Hedrick et al. |
| 7,744,820 B2 | 6/2010 | Togawa et al. |
| 7,780,649 B2 | 8/2010 | Shippert |
| 7,789,872 B2 | 9/2010 | Shippert |
| 7,794,449 B2 | 9/2010 | Shippert |
| 8,062,286 B2 | 11/2011 | Shippert |
| 8,100,874 B1 | 1/2012 | Jordan et al. |
| 8,293,532 B2 | 10/2012 | Moynahan |
| 8,333,740 B2 | 12/2012 | Shippert |
| 8,409,860 B2 | 4/2013 | Moynahan |
| 8,622,997 B2 | 1/2014 | Shippert |
| 8,632,498 B2 | 1/2014 | Rimsa et al. |
| 9,259,379 B2 | 2/2016 | Corcoran-Henry et al. |
| 9,278,165 B2 | 3/2016 | Park et al. |
| 2002/0188280 A1 | 12/2002 | Nguyen et al. |
| 2004/0005246 A1 | 1/2004 | Efthimiadis et al. |
| 2004/0097829 A1 | 5/2004 | McRury et al. |
| 2005/0084961 A1 | 4/2005 | Hedrick et al. |
| 2006/0184119 A1 | 8/2006 | Remde et al. |
| 2006/0224144 A1 | 10/2006 | Lee |
| 2007/0106208 A1 | 5/2007 | Uber et al. |
| 2009/0287190 A1 | 11/2009 | Shippert |
| 2009/0299328 A1 | 12/2009 | Mudd et al. |
| 2010/0174162 A1 | 7/2010 | Gough et al. |
| 2010/0268189 A1 | 10/2010 | Byrnes et al. |
| 2011/0009822 A1 | 1/2011 | Nielsen |
| 2011/0198353 A1 | 8/2011 | Tsao |
| 2013/0131635 A1 | 5/2013 | Rimsa et al. |
| 2013/0150825 A1 | 6/2013 | Rimsa et al. |
| 2013/0158515 A1 | 6/2013 | Austen, Jr. |
| 2013/0324966 A1 | 12/2013 | Park et al. |
| 2014/0017206 A1 | 1/2014 | Barere et al. |
| 2014/0081237 A1 | 3/2014 | Wolters et al. |
| 2015/0374888 A1 | 12/2015 | Shippert |

FOREIGN PATENT DOCUMENTS

| | | |
|---|---|---|
| WO | 2012/083412 A1 | 6/2012 |
| WO | 2012/109603 A1 | 8/2012 |
| WO | 2012/139593 A2 | 10/2012 |
| WO | 2013/106655 A1 | 7/2013 |

OTHER PUBLICATIONS

International Preliminary Report on Patentability for Application No. PCT/US2016/018444, dated Aug. 31, 2017. 10 pages.

Coleman et al.; "Fat Grafting to the Breast Revisited: Safety and Efficacy;" Plastic and Reconstructive Surgery; 119 (3):775-785 (Mar. 2007).

Delay et al.; "Fat Injection to the Breast: Technique, Results and Indications Based on 880 Procedures Over 10 Years;" Aesthetic Surgery Journal; 29(5):360-376 (Sep./Oct. 2009).

Pakhomov et al.; "Hydraulically Coupled Microejection Technique for Precise Local Solution Delivery in Tissues;" J. Neurosci Methods; 155(2):231-240 [Abstract] (Sep. 15, 2006).

Smith et al.; "Autologous Human Fat Grafting: Effect of Harvesting and Preparation Techniques on Adipocyte Graft Survival;" Plastic and Reconstructive Surgery; 117(6):1836-1844 (2006).

Ting et al.; "A New Technique to Assist Epidural Needle Placement;" Anesthesiology; 112(5):1128-1135 (May 2010).

Yoshimura et al.; "Cell-Assisted Lipotransfer for Cosmetic Breast Augmentation: Supportive Use of Adipose-derived Stem/Stromal Cells;" Aesthetic Plastic Surgery Journal; 32:48-55 (2008).

TISSUE PROCESSING DEVICE AND ASSOCIATED SYSTEMS AND METHODS

This application is a continuation of U.S. patent application Ser. No. 15/047,034 (issued as U.S. Pat. No. 10,184,111), filed Feb. 18, 2016, which itself claims the benefit under 35 USC § 119(e) of U.S. Provisional Patent Application No. 62/118,192, filed on Feb. 19, 2015, each of which is herein incorporated by reference in its entirety.

The present disclosure relates to tissue processing devices, and more particularly, to tissue processing devices for collection, processing, preparation, and transfer of biological material including adipose tissue for use in fat grafts during harvest, processing, and transplantation.

Various products are used for harvesting, processing, and transplanting biological material such as, for example, human adipose tissue. Such products, however, may require multiple mechanical transfers of the biological material from one device to another. For example, the biological material is generally transferred between one or more processing devices, and further transferred to a different apparatus before ultimate transfer into an implantation site.

During each of the processing and transplantation steps, forces, e.g., shear forces, are exerted on the biological material. Due to the multiple transfers of the biological material, the biological material is subjected to an increasing amount of shear forces, which can negatively affect the viability of the biological material. As such, the viability of the biological material can be substantially reduced by manipulation during collection, processing, and implantation.

In addition, due to the different steps involved in harvesting, processing, and transplanting the biological material, the process of obtaining the biological material can be tedious and extensive. In particular, the process involves several steps using different pieces of equipment, thereby increasing the time and cost for obtaining the biological material and further increasing the risk of reducing the viability of the biological material.

Improved systems are therefore needed to overcome possible shortcomings with current tissue transfer devices. Accordingly, tissue processing devices, as well as associated systems and methods, are provided.

According to certain embodiments, a tissue processing device is, therefore, provided. The tissue processing device can include a body including a cavity formed therein. The body defines a proximal end and a distal end. The tissue processing device can include a tissue collection port formed in a wall of the body adapted to receive tissue therethrough and in fluid communication with the cavity. The tissue processing device can include a rotary transfer device including a helical blade for transferring the tissue from the proximal end to the distal end of the body. The tissue processing device can include a port, e.g., an extrusion port, a removal port, or the like, formed in the body adapted for removal therethrough of the tissue from the cavity.

The cavity can include a first compartment and a second compartment. In certain embodiments, the first compartment can include a cylindrical shape having a longitudinal axis extending from the proximal end towards the distal end.

The tissue collection port and the extrusion port can be in fluid communication with the first compartment. In certain embodiments, the tissue processing device can include at least one injection port in fluid communication with the cavity and adapted for injection of a wash solution therethrough. In certain embodiments, the tissue processing device can include a vacuum port in fluid communication with the second compartment.

The first compartment and the second compartment can be separated from each other by a filter. In certain embodiments, the filter can include a mesh wall.

During transfer of the tissue from the proximal end to the distal end of the body, undesired components can be passed through the filter and transferred from the first compartment to the second compartment for subsequent disposal. In particular, during transfer of the tissue from the proximal end to the distal end of the body, the tissue is processed and cleaned for transplantation.

In certain embodiments, the rotary transfer device can be rotatably disposed within the first compartment. In certain embodiments, the tissue processing device can include a manual crank for rotatably driving the rotary transfer device. In certain embodiments, the tissue processing device can include an automated actuation means, e.g., a graphical user interface, a motor, a processing device, combinations thereof, or the like, for rotatably driving the rotary transfer device.

In certain embodiments, the transfer device can include an auger. In certain embodiments, the transfer device can include at least one catcher extending from a rotatable shaft.

The body and the transfer device can provide a low-shear environment for adipose tissue of the tissue. In certain embodiments, the adipose tissue can be human adipose tissue.

According to certain embodiments, a method of processing tissue is provided. The method includes providing a tissue processing device as described herein. The method can include introducing tissue for processing through a tissue collection port and into the cavity of the tissue processing device. The method can include transferring the tissue from a proximal end to a distal end of a body of the tissue processing device with a rotary transfer device. The method can include removing the tissue from a port and out of the tissue processing device after the tissue has been processed.

In certain embodiments, the method can include injecting a wash solution into the body through at least one injection port formed in the body to clean and process the tissue. The method can include rotatably driving the rotary transfer device with a manual crank. The method can include rotatably driving the rotary transfer device with an automated actuation means.

The method can include filtering the tissue of undesired components through a filter during transfer of the tissue from the proximal end to the distal end of the body. The method can include removing the undesired components from the second compartment through a vacuum port formed in the second compartment.

According to certain embodiments, a system of tissue processing is provided. The system includes a tissue processing device as described herein. The system can include a source of the tissue for introduction of the tissue into the tissue collection port. The system can include an injection device for removal of the tissue from the port.

In certain embodiments, the system can include a source of wash solution for introduction into the cavity through an injection port formed in the body. In certain embodiments, the system can include a vacuum source for removing undesired components from the second compartment through a vacuum port. In certain embodiments, the system can include an automated actuation means for rotatably driving the rotary transfer device.

According to certain embodiments, a tissue processing device is provided. The tissue processing device includes a body including a cavity formed therein. The body defines a proximal end and a distal end. The tissue processing device can include a tissue collection port formed in a wall of the body adapted to receive tissue therethrough and in fluid communication with the cavity. The tissue processing device can include an auger including a blade for transferring the tissue from the proximal end to the distal end of the body. The tissue processing device can include a removal port formed in the body adapted for withdrawal therethrough of the tissue from the cavity.

In certain embodiments, the auger can be rotatably disposed within a first compartment of the body. In certain embodiments, the tissue processing device includes a crank for rotatably driving the auger. In certain embodiments, the tissue processing device includes an automated actuation means for rotatably driving the auger.

The auger can include a rotary transfer device. In certain embodiments, the auger can include at least one catcher extending from a rotatable shaft. In certain embodiments, the auger can include a helical blade.

According to certain embodiments, a method of processing tissue is provided. The method includes providing a tissue processing device as described herein. The method includes introducing tissue for processing through a tissue collection port and into a cavity of the tissue processing device. The method includes transferring the tissue from the proximal end to the distal end of the body with an auger. The method includes withdrawing the tissue from the cavity through a removal port after the tissue has been processed. The methods include rotatably driving the auger, e.g., manually, via automated means, or the like.

According to certain embodiments, a system of tissue processing is provided. The system includes a tissue processing device as described herein. The system includes a source of the tissue for introduction of the tissue into the tissue collection port of the tissue processing device. The system includes an injection device for removal of the tissue from the removal port. In certain embodiments, the system includes an automated actuation means for rotatably driving the auger.

The tissue can thereby be processed and transferred in a closed and continuous environment, thereby providing for a low-shear environment which increases the viability of the tissue.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products or compositions for treating patients. For example, various biological products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such biological products can include, for example, adipose tissue for use in fat grafts. The viability of the biological products is essential in successfully treating patients.

Figure 1:
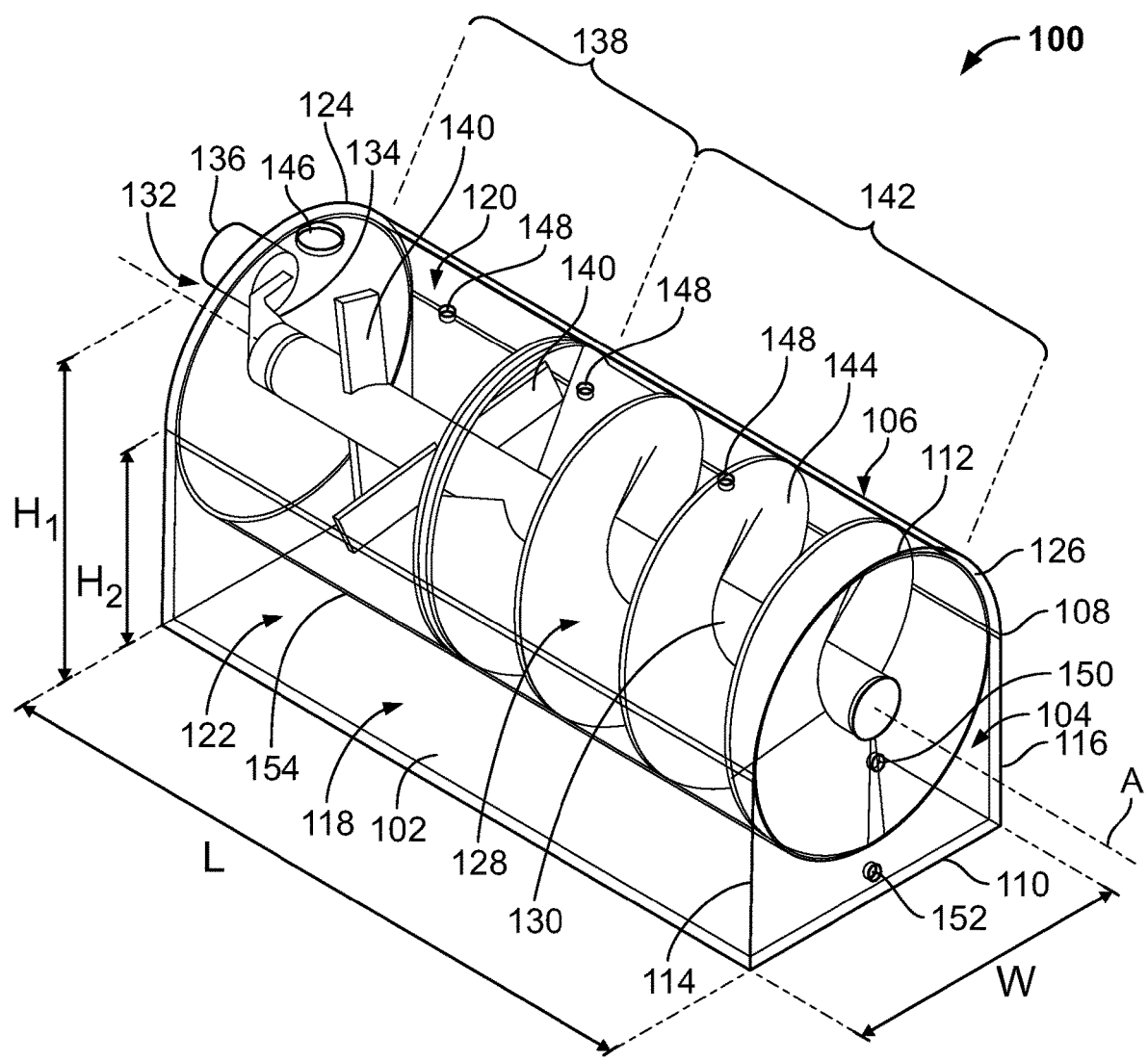
FIG. 1 is a perspective view of a tissue processing device, according to certain embodiments.
Figure 2:
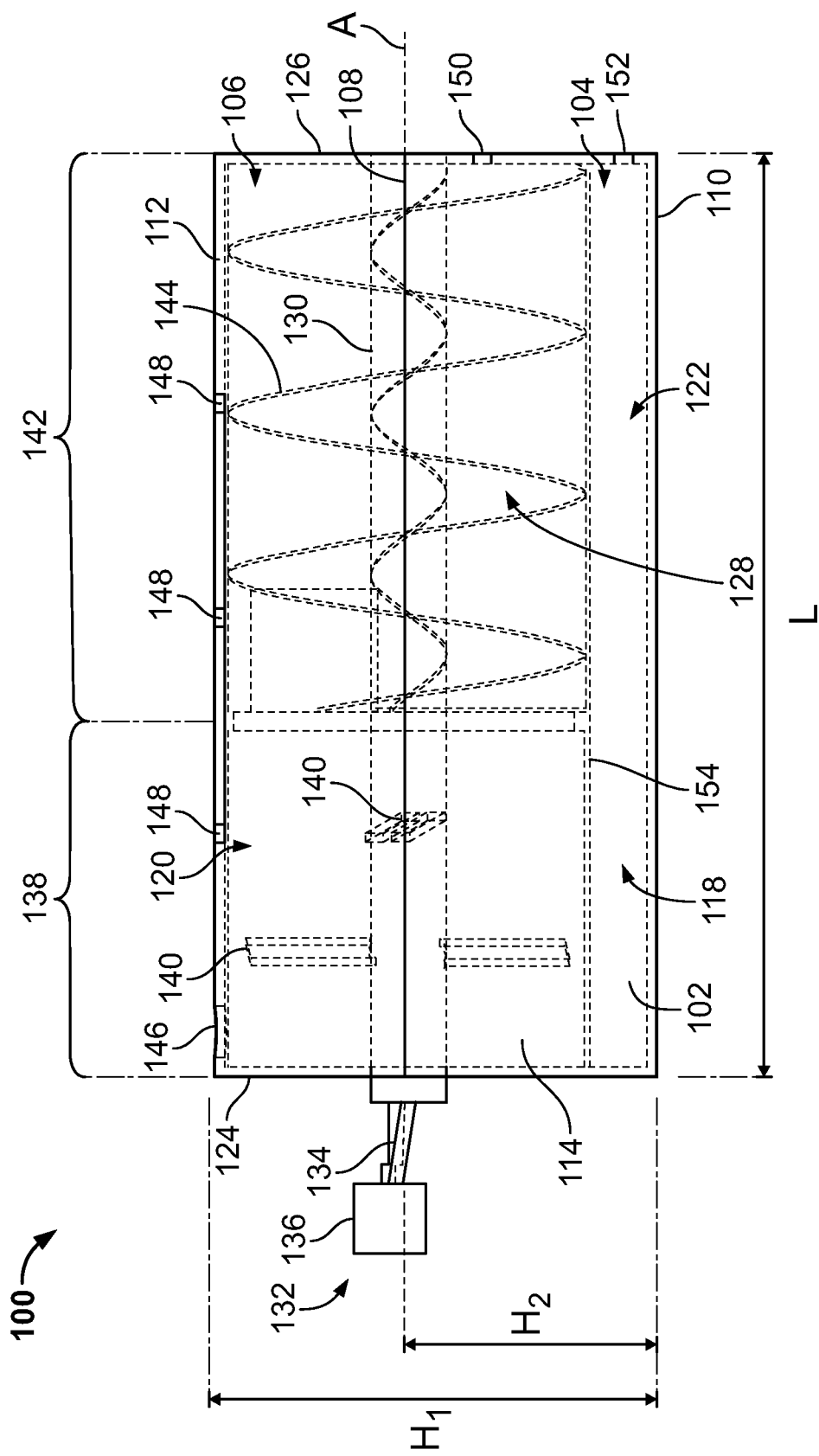
FIG. 2 is a side view of a tissue processing device, according to certain embodiments.
Figure 3:
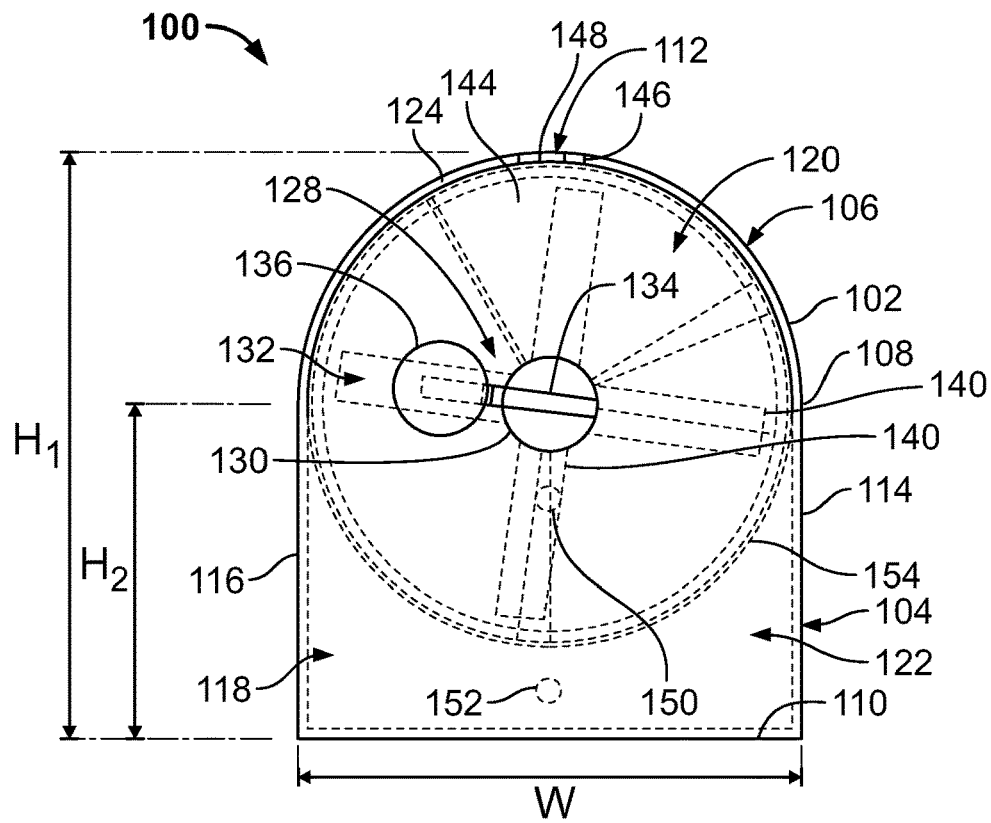
FIG. 3 is a front view of a tissue processing device, according to certain embodiments.
Figure 4:
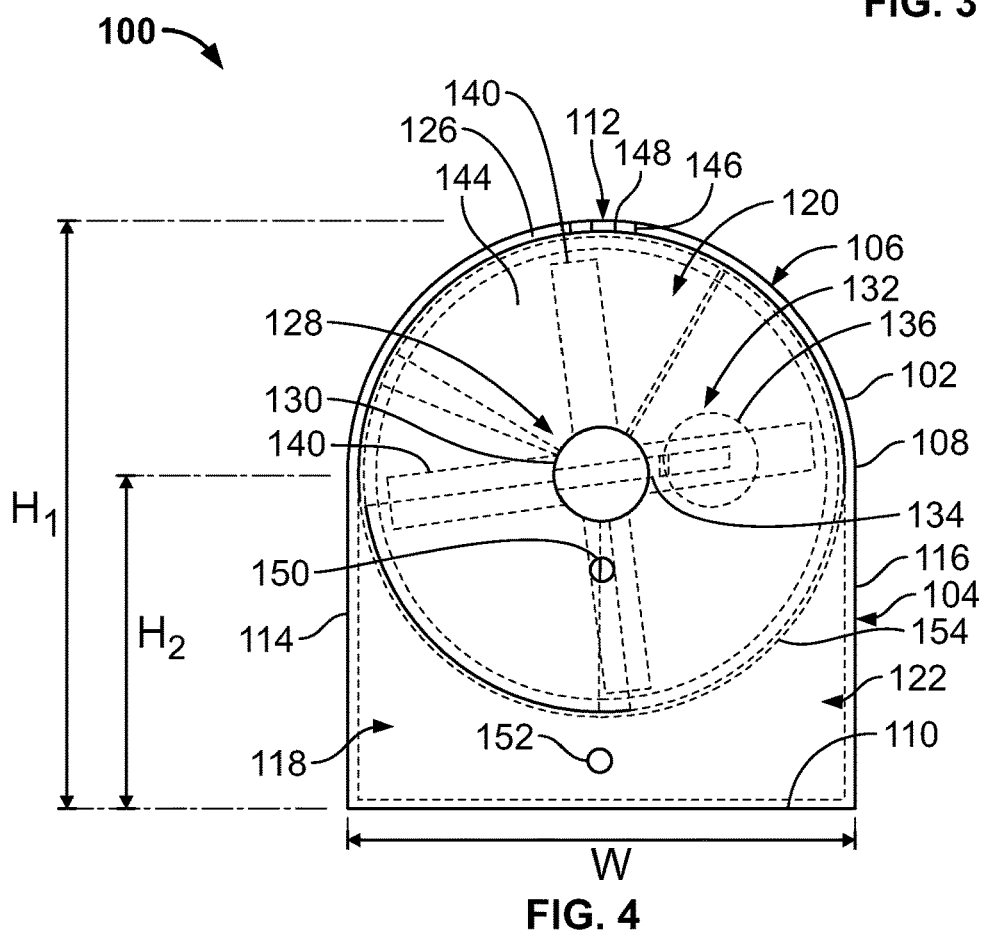
FIG. 4 is a rear view of a tissue processing device, according to certain embodiments.

With reference to FIGS. 1-4, various embodiments of an exemplary tissue processing device 100 is provided. For example, FIG. 1 shows a perspective view, FIG. 2 shows a side view, FIG. 3 shows a front view, and FIG. 4 shows a rear view of the tissue processing device 100.

The tissue processing device 100 includes a body 102, e.g., a processing canister, defining a width W, a length L, and a height $H_1$. The body 102 includes a bottom portion 104 and a top portion 106. In some embodiments, the body 102 can be transparent or semi-transparent to allow visualization of tissue during processing. In some embodiments, the body 102 can be translucent. The bottom portion 104 defines base portion having, for example, a substantially rectangular or square configuration, and the top portion 106 defines a substantially circular or cylindrically shaped configuration. The bottom portion 104 and the top portion 106 connect at a connecting line or region 108 such that the body 102 transitions from the rectangular or square configuration to the circular configuration. The connecting region 108 can be at a height $H_2$ relative to the bottom surface 110.

The bottom surface 110 of the body 102 can be flat and configured for placement on a working surface, and the top surface 112 of the body 102 can be round or circular. First and second sides 114, 116 of the body 102 can initially be flat (e.g., perpendicular to the bottom surface 110) and transition to a round or circular configuration at the connecting region 108.

The interior of the body 102 includes a hollow space or cavity 118 formed therein. The cavity 118 can be separated into a first compartment 120 and a second compartment 122 adjacently disposed relative to each other. In certain embodiments, as will be described in greater detail below, the first and second compartments 120, 122 can be separated by a filter 154. The first compartment 120 can define a substantially cylindrical configuration extending from a front surface 124 (e.g., a proximal end) to a rear surface 126 (e.g., a distal end) along the length L of the body 102.

The first compartment 120 can be configured and dimensioned to rotatably receive therein an auger 128, e.g., an auger pump, a rotary transfer device, a mechanical transfer device, or the like. Although illustrated as an auger 128, in certain embodiments the first compartment 120 can include an alternative low-shear rotary pump, e.g., a progressing cavity pump(s), multiple rotor screw pumps, lobe pumps, combinations thereof, or the like. The auger 128 includes a shaft 130 extending between the front and rear surfaces 124, 126 of the body 102. In certain embodiments, the height at which the shaft 130 is positioned can be similar to the height $H_2$ for the connecting point 108. For example, the axis A of rotation of the shaft 130 can extend at a height $H_2$ relative to the bottom surface 110. In addition, the axis A of rotation of the shaft 130 can be substantially parallel to the plane defined by the bottom surface 110.

The auger 128 includes a crank 132 connected to a distal end of the shaft 130 and extending from an outer portion of the front surface 124. In particular, the crank 132 extends outside of the body 102. The crank 132 includes an extension 134 diagonally extending from the axis A of the shaft 130 and a grip portion 136. In certain embodiments, the grip portion 136 can be fixedly secured to the extension 134. In certain embodiments, the grip portion 136 can be rotatably secured to the extension 134. Thus, rotation of the crank 132 rotates the shaft 130 about the axis A.

Although illustrated as adapted for manual actuation of the auger 128, in certain embodiments, the auger 128 can be automated. In certain embodiments, rather than including a crank 132, the tissue processing device 100 can include an automated actuation means communicatively connected to the auger 128 for rotatably driving the auger 128. For example, the tissue processing device 100 can include a graphical user interface (GUI) connected to a computer or a processing device and a motor configured to receive input regarding actuation of the auger 128. Alternatively, the auger 128 can be coupled to a motor with simple on/off switches or speed controls.

The auger 128 can include a first section 138 at a portion proximal to the front surface 124 and can includes one or more catchers 140, e.g., paddles, attached to the first section 138. The catchers 140 can be configured and dimensioned to engage collagen or fiber during processing of the biological material. The first section 138 can extend along only a portion of the length of the shaft 130. The catchers 140 can extend on opposing sides of the shaft 130 in a substantially perpendicular manner.

In certain embodiments, the catchers 140 can have a substantially rectangular shape. In certain embodiments, the catchers 140 can define an oval shape. In certain embodiments, the catchers 140 can be substantially planar or linear in extension. In certain embodiments, the catchers 140 can be curved. In certain embodiments, the catchers 140 can be positioned substantially parallel to the front surface 124. In certain embodiments, the catchers 140 can be positioned at an angle relative to the front surface 124. In embodiments including two or more catchers 140, the angular position of the catchers 140 can be offset relative to each other (e.g., by 90°, as shown in FIG. 1). In certain embodiments, a plurality of catchers 140 can be evenly spaced relative to each other in a circumferential manner.

The auger 128 further includes a second section 142 at a portion distal to the front surface 124 including a helical blade(s) 144, e.g., a helical screw blade(s), a rotating screw (s), or the like. The blade 144 can extend along only a portion of the length of the shaft 130. For example, the blade 144 can extend between the first section 138 and an inner portion of the rear surface 126 of the body 102. During rotation of the blade 144, the blade 144 can assist with the transfer, active wash, extrusion or removal into injection syringes, combinations thereof, or the like, of the biological material contained within the device 100. In particular, during rotation of the blade 144, the biological material can be translated or pumped along the length of the first compartment 120 by forces imparted by the blade 144. Thus, the first compartment 120 can represent the space or volume through which the biological material is transported with the auger 128.

In certain embodiments, characteristics of the auger 128 can be modified or varied to control the amount of shear force imparted on the biological material. For example, the characteristics can be, e.g., the shape of the blade 144, the size of the blade 144, the seal or spacing between the auger 128 and the inner walls of the first compartment 120 such that slip of the biological material is prevented or reduced, the pitch of the auger 128, the rate of rotation of the auger 128, a snap clutch associated with the drive shaft, combinations thereof, or the like.

As noted above, a filter 154 can separate the first and second compartments 120, 122 within the body 102. In particular, the filter 154 can define at least a portion of the wall surrounding the auger 128. For example, the filter 154 can separate the blade 144 and/or the catchers 140 (or both) from the second compartment 122 along the bottom of the first compartment 120. In certain embodiments, the filter 154 can be configured as a mesh filter. It should be understood that the pore size of the mesh filter 154 can be optimized for cleaning the desired biological material. For example, the pore size can be adjusted for removing blood and undesired components from the adipose tissue before reimplantation of the adipose tissue. Thus, as the adipose tissue travels through the first compartment 120, the adipose tissue can be cleaned, and the undesired components can pass through the filter 154 and into the second compartment 122 for subsequent disposal.

The first compartment 120 can include one or more collection ports 146, e.g., adipose collection ports, openings, or the like, for introduction of the biological material into the first compartment 120. The collection ports 146 can pass through the wall of the first compartment 120 and into the cavity formed within the first compartment 120. The collection ports 146 can be positioned adjacent to the front surface 124 such that biological material introduced through the collection port 146 enters the first section 138 of the first compartment 120. In certain embodiments, the biological material can be introduced into the first section 138 of the first compartment 120 by applying a suction through the port 152, e.g., a vacuum port, to pull the biological material through the collection port 146. In certain embodiments, the biological material can be introduced into the first section 138 of the first compartment 120 by, e.g., pumping the biological material into the collection port 146, injecting the biological material into the collection port 146, combinations thereof, or the like.

The first compartment 120 further includes one or more injection ports 148, e.g., openings, for introduction of a wash solution into the first compartment 120. The injection ports 148 can pass through the wall of the first compartment 120 and into the cavity formed within the first compartment 120. In certain embodiments, at least one of the injection ports 148 can be positioned over the first section 138 of the first compartment 120 and at least one of the injection ports 148 can be positioned over the second section 142 of the first compartment 120 such that the wash solution can be selectively introduced into the first section 138, the second section 142, or both.

In certain embodiments, the wash solution can be selected from, e.g., a crystalloid solution, sterile saline solution, a detergent, ringer's lactate, collagenase, stem cells, pH buffers, combinations thereof, or the like. Non-exclusive examples of detergents useful in the methods of the present disclosure include TWEEN® and TRITON-X®. In certain embodiments, the wash solution can include common soaps formed of synthetic surfactants and/or animal derived surfactants (e.g., tallow). In certain embodiments, the wash solution can be nonionic. In certain embodiments, the wash solution can comprise a biocompatible detergent. In certain embodiments, the wash solution can comprise a surfactant that is not a poloxamer. In certain embodiments, alternative wash solutions can be used, such as the wash solutions described in U.S. patent application Ser. Nos. 13/894,912 and 13/929,252, the entirety of which is incorporated herein by reference.

In certain embodiments, the collection port 146, the injection port 148, or both, can be aligned along the top surface 112 of the body 102. In certain embodiments, the collection port 146, the injection port 148, or both, can be offset from the top surface 112 of the body 102.

The first compartment 120 includes one or more extrusion ports 150, e.g., extraction openings, removal openings, withdrawal openings, or the like, passing through the wall of the rear surface 126 and into the cavity formed within the first compartment 120. The extrusion ports 150 can be positioned at a portion of the rear surface 126 below the shaft 130 of the auger 128, e.g., between the shaft 130 and the filter 154. In certain embodiments, the extrusion ports 150 can be aligned below the axis A for the shaft 130. In certain embodiments, the extrusion ports 150 can be used to fluidically connect the first compartment 120 to an injection device, e.g., a syringe or cannula, and fill the injection device with adipose tissue within the first compartment 120.

In certain embodiments, the second compartment 122 can include one or more ports 152, e.g., openings, passing through the wall of the rear surface 126 and into the cavity formed within the second compartment 122. The ports 152 can be a vacuum port which connects to a wash and/or waste canister and a vacuum source for cleaning the second compartment 122. The ports 152 can be positioned at a portion of the rear surface 126 between the filter 154 and the bottom surface 110. In certain embodiments, rather than or in addition to the ports 152, at least a portion of the bottom surface 110 can be removably connected to the second compartment 122 to allow cleaning of the waste collected in the second compartment 122.

Figure 5:
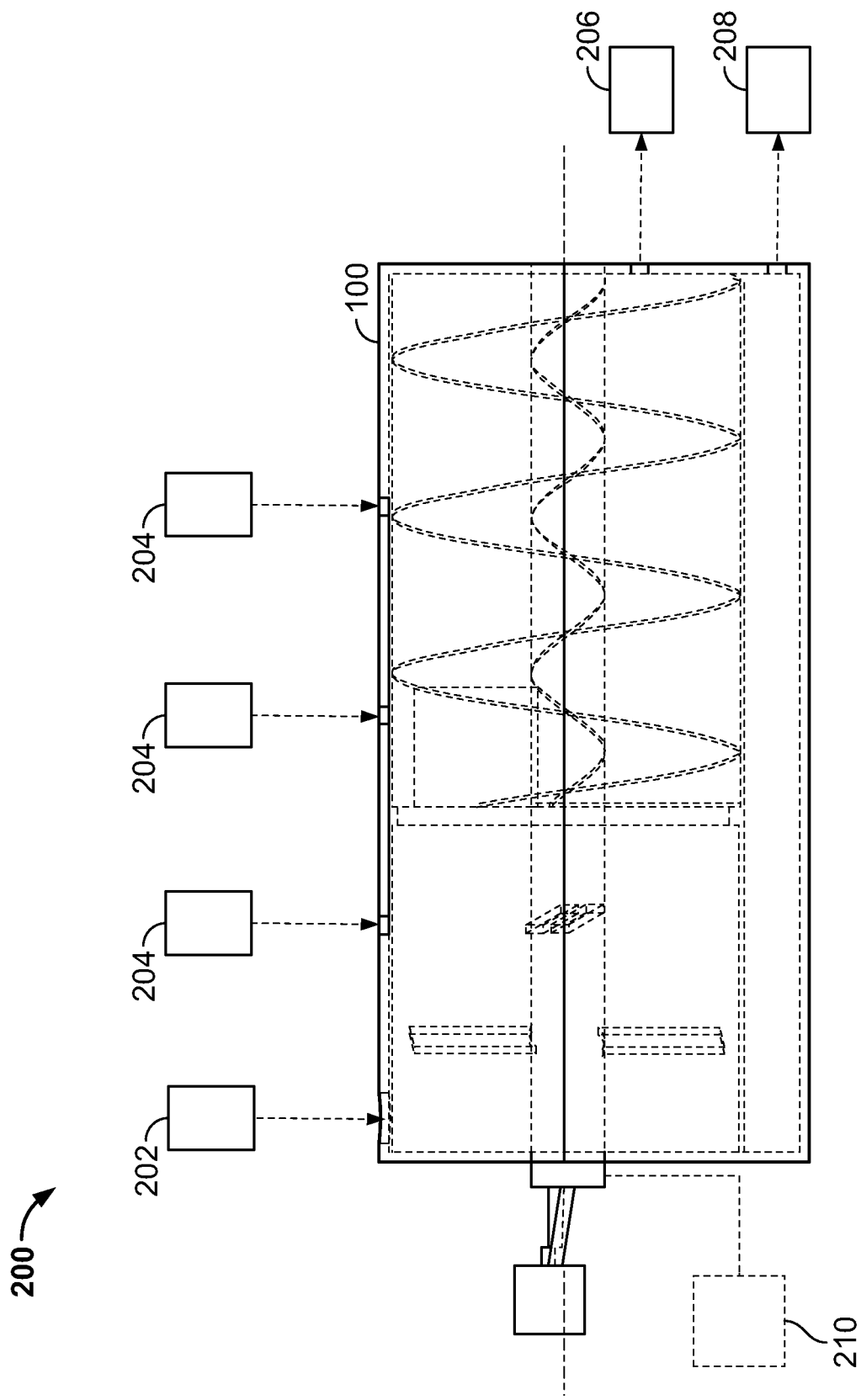
FIG. 5 is a diagrammatic view of a tissue processing system including a tissue processing device, according to certain embodiments.

With reference to FIG. 5, a diagrammatic view of an exemplary tissue processing system 200 including the tissue processing device 100 is provided. The system 200 includes a source of harvested biological material 202, one or more sources of wash solution 204, an injection device 206, and a vacuum source 208. The biological material can be introduced into the first compartment 120 through the port 146 from the source of harvested biological material 202.

The wash solution can be introduced into the first section 138, the second section 142, or both, of the first compartment 120 through the ports 148 from the source of wash solution 204. Although illustrated as three separate sources of wash solution 204, in certain embodiments, the wash solution can be in, e.g., one, two, three, four, or the like, sources. In certain embodiments, one or more types of wash solution can be used. For example, in embodiments having two type of wash solutions, one source of wash solution 204 can contain the first type of wash solution and another source of wash solution 204 can contain the second type of wash solution, thereby maintaining separation between the two types of wash solution.

The injection device 206, e.g., a syringe, can be used to withdraw the processed biological material from the first compartment 120 through the port 150. The vacuum source 208, e.g., a pump, can be connected to the port 152 to withdraw the undesired materials from the second compartment 122, thereby cleaning the tissue processing device 100. In certain embodiments, a cleaning solution can be introduced into the second compartment 122 through the port 152 to clean the second compartment 122.

In certain embodiments, the system 200 can include automated actuation means 210, e.g., a motor, a processing device, a graphical user interface, combinations thereof, and the like, for automated regulation of the auger 128. For example, in addition to or rather than including a manual crank 132, the tissue processing device 100 can include the automated actuation means 210 communicatively connected thereto. The automated actuation means can include a simple motor attached to an on/off switch or speed control.

In operation, first and second compartments 120, 122 can serve as a processing canister for processing biological material, such as adipose tissue. Although discussed herein as being used for processing adipose tissue harvested from a human patient, it should be understood that the exemplary tissue processing device 100 can be used for processing a variety of different biological materials, including non-human tissue. The first and second compartments 120, 122 can be adapted to serve for the collection and post-collection processing of the adipose tissue.

In certain embodiments, the tissue processing device 100 can be operated in an orientation defined by placement of the tissue processing device 100 onto the first or second side 114, 116 such that the cylindrical first compartment 120 is turned on its side and the front and rear surfaces 124, 126 are perpendicular to the surface on which the tissue processing device 100 is positioned. The washing and transport steps of processing the adipose tissue can be accomplished with increased efficiency in this orientation. For example, in such orientations, gravity can assist with removal of the adipose tissue wash waste, final adipose tissue transfer into external injection devices, or both.

In certain embodiments, the tissue processing device 100 can be positioned with the bottom surface 110 facing downward. In certain embodiments, the tissue processing device 100 can be configured for vertical operation or horizontal operation. The harvested adipose tissue can be introduced at a proximal end of the tissue processing device 100 through the port 146 and is transported through the tissue processing device 100 by the auger 128. For example, during rotation of the auger 128, the blades 144 can push the adipose tissue along the length of the first compartment 120 up to the inner portion of the rear surface 128.

In certain embodiments, a tissue wash solution can be introduced into the first section 138, the second section 142, or both, of the first compartment 120 to rinse the adipose tissue as the adipose tissue is transported along the length L of the first compartment 120 and in the direction of the port 150 for transferring the processed adipose tissue into the injection device. As discussed above, the tissue processing device 100 includes first and second compartments 120, 122. The first compartment 120 can house the auger 128 and collects the harvested adipose tissue in the first section 138, e.g., the entrance portion. The second compartment 122 can collect waste and excess wash solution as the adipose tissue is transported and rinsed through the auger 128.

The auger 128 can be adapted to serve as a low-shear mechanism for processing and transportation of the adipose tissue from harvest to transplantation. In particular, upon introduction into the first section 138 of the first compartment 120, adipose tissue harvested from a patient can be mechanically pushed through the length L of the tissue processing device 100. In certain embodiments, the auger 128 can be actuated to push the adipose tissue using a manual crank 132. In certain embodiments, the auger 128 can be actuated to push the adipose tissue through automated means.

The walls surrounding at least a portion of the auger 128 can be formed as a filter 154 having a mesh material, the pore size of which can be optimized to filter waste, blood, undesired components, or combinations thereof, from the adipose tissue wash. In particular, rotation of the auger 128 can mechanically transport the adipose tissue through and along the auger 128 from the proximal end to the distal end of the tissue processing device 100.

Tissue wash solution can be injected into the first compartment 120, passed around the adipose tissue for cleaning the adipose tissue, and flushed through the mesh walls of the filter 154 to wash the adipose tissue in preparation for transplantation. The cleaned adipose tissue can be passed along the auger 128 up to the inner area of the first compartment 120 adjacent to the rear surface 126 (cleaning undesired components through the filter 154 along the way), at which point the cleaned adipose tissue can be collected for extrusion or removal into an injection device. For example, the cleaned adipose tissue can be extruded from the port 150 to fill an attached injection device, e.g., a syringe. In certain embodiments, an injection device can be connected to the port 150 and the auger 128 can be actuated to mechanically push the processed and cleaned adipose tissue into a compartment of the injection device. In certain embodiments, a needle of the injection device can be inserted at least partially into the port 150 and the adipose tissue can be extruded into the injection device using the suction created by the plunger of the injection device.

In certain embodiments, the tissue processing device 100 can be used as a storage device for the cleaned adipose tissue until the cleaned adipose tissue is needed. When ready for use, the cleaned adipose tissue can be extruded from the tissue processing device 100 with an injection device. In certain embodiments, the cleaned adipose tissue can be extruded from the tissue processing device 100 directly into an implantation device or into a storage container.

The second compartment 122 containing, e.g., waste, blood, undesired components, combinations thereof, or the like, can be cleaned by connecting a vacuum source, a wash/waste canister, or both, to the port 152. The waste within the second compartment 122 can be extruded out of the port 152 to remove the undesired substances from the tissue processing device 100. In certain embodiments, the second compartment 122 can be flushed with a cleaning solution introduced through the port 152 to further clean the second compartment 122.

The tissue processing device 100 discussed herein simplifies the processing steps required for adipose tissue transplantation by combining processing with tissue transfer into an injection device. In particular, the tissue processing device 100 provides a closed, low-shear, and continuous process that minimizes the number of mechanical adipose tissue transfers, thereby reducing the negative effects on adipose tissue viability.

Specifically, the tissue processing device 100 increases adipose tissue graft viability and improves treatment outcomes by reducing the steps needed for adipose tissue transfer between a processing device and a syringe, between a syringe and a syringe, or both, by reducing processing steps involved in preparation for adipose tissue transplantation, and by controlling forces exerted on the adipose tissue, including a reduction in shear forces. The tissue processing device 100 therefore simplifies and shortens the duration of procedure for adipose transplantation or fat grafting by providing an efficient and easy-to-use processing device.

Although the devices and methods of the present disclosure have been described with reference to exemplary embodiments thereof, the present disclosure is not limited to such exemplary embodiments and or implementations. Rather, the devices and methods of the present disclosure are susceptible to many implementations and applications, as will be readily apparent to persons skilled in the art from the disclosure hereof. The present disclosure expressly encompasses such modifications, enhancements and or variations of the disclosed embodiments. Since many changes could be made in the above exemplary embodiments and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A tissue processing device, comprising:
    a body including a cavity formed therein, the cavity comprising a first cylindrical compartment and a second compartment, and the body defining a proximal section and a distal section;
    a tissue collection port formed in a wall of the body proximal section and adapted to receive tissue therethrough and in fluid communication with the cavity;
    at least one injection port formed in fluid communication with the cavity;
    a rotary transfer device comprising a helical blade and at least one catcher extending from a rotatable shaft of the rotary transfer device;
    an automated actuation unit for rotatably driving the rotary transfer device;
    a filter separating the first cylindrical compartment from the second compartment, wherein the filter defines at least a portion of a wall surrounding the rotary transfer device; and
    an extrusion port formed in a wall of the body distal section and adapted for removal therethrough of the tissue from the cavity.

2. The tissue processing device of claim 1, wherein the tissue collection port and the extrusion port are in fluid communication with the first cylindrical compartment.

3. The tissue processing device of claim 1, wherein the helical blade is disposed within the first cylindrical compartment for transferring the tissue from the body proximal section to the body distal section.

4. The tissue processing device of claim 1, wherein the at least one injection port comprises:
    a first injection port formed in the wall of the body proximal section; and
    second and third injection ports formed in a wall of the body distal section.

5. The tissue processing device of claim 4, wherein the first, second, and third injection ports are in fluid communication with the cavity and adapted for injection of a wash solution therethrough.

6. The tissue processing device of claim 4, wherein the first, second, and third injection ports are in fluid communication with the cavity and adapted for injection of a clean solution therethrough.

7. The tissue processing device of claim 1, comprising a vacuum port formed in the wall of the body distal section, the vacuum port being in fluid communication with the second compartment.

8. The tissue processing device of claim 1, wherein the body is formed from a transparent or semi-transparent material to allow for visualization of tissue during processing.

9. The tissue processing device of claim 1, wherein the automated actuation unit comprises:
a graphical user interface connected to a computer or at least one processor; and
a motor configured to receive input regarding information related to actuation of the rotary transfer device.

10. A method of processing tissue, comprising:
providing a tissue processing device, the tissue processing device including:
a body including a cavity formed therein, the cavity comprising a first cylindrical compartment and a second compartment, and the body defining a proximal section and a distal section;
a tissue collection port formed in a wall of the body proximal section and in fluid communication with the cavity;
at least one injection port formed in fluid communication with the cavity;
a rotary transfer device including a helical blade and at least one catcher extending from a rotatable shaft of the rotary transfer device;
an automated actuation unit for rotatably driving the rotary transfer device;
a filter separating the first cylindrical compartment from the second compartment, wherein the filter defines at least a portion of a wall surrounding the rotary transfer device; and
an extrusion port formed in a wall of the body distal section;
introducing tissue for processing through the tissue collection port of the body proximal section and into the cavity;
actuating the rotary transfer device to transfer the tissue from the body proximal section to the body distal section; and
removing the tissue from the cavity through the extrusion port after the tissue has been processed.

11. The method of claim 10, wherein the tissue collection port and the extrusion port are in fluid communication with the first cylindrical compartment.

12. The method of claim 10, wherein the helical blade is disposed within the first cylindrical compartment for transferring the tissue from the body proximal section to the body distal section.

13. The method of claim 10, wherein the at least one injection port comprises:
a first injection port formed in the wall of the body proximal section; and
second and third injection ports formed in a wall of the body distal section.

14. The method of claim 13, further comprising injecting a wash solution into the cavity through the first, second, or third injection ports after introducing the tissue through the tissue collection port, and prior to removing the tissue from the extrusion port, to clean and process the tissue for transplantation.

15. The method of claim 10, further comprising filtering the tissue of undesired components through the filter during transfer of the tissue from the body proximal section to the body distal section.

16. The method of claim 10, further comprising extruding undesired components from the second compartment through a vacuum port formed in a wall of the body distal section prior to removing the tissue from the cavity.

17. The method of claim 10, wherein the extrusion port is adapted to fluidically connect the first cylindrical compartment to an injection device and fill the injection device with processed adipose tissue within from first compartment.

18. The method of claim 17, wherein the injection device is a syringe or cannula.

19. The method of claim 10, wherein the tissue is human adipose tissue.

20. The method of claim 10, wherein the automated actuation unit comprises:
a graphical user interface connected to a computer or at least one processor; and
a motor configured to receive input regarding information related to actuation of the rotary transfer device.

* * * * *